United States Patent [19]

Leigh

[11] 4,153,160
[45] May 8, 1979

[54] DISPOSABLE SLIDE-STEP PERCUTANEOUS TRANSHEPATIC CHOLANGIOGRAPHY PROCEDURE TRAY

[75] Inventor: Kay K. Leigh, White Bear Lake, Minn.

[73] Assignee: Johannah Medical Services, Inc., Minneapolis, Minn.

[21] Appl. No.: 873,389

[22] Filed: Jan. 30, 1978

[51] Int. Cl.² .................. B65D 1/34; A45C 11/26
[52] U.S. Cl. ...................... 206/370; 206/570; 206/564; 220/345
[58] Field of Search ............. 206/370, 570, 564; 220/23.8, 23.6, 356, 345

[56] References Cited

U.S. PATENT DOCUMENTS

| | | | |
|---|---|---|---|
| 2,035,340 | 3/1936 | Primavera | 220/345 |
| 3,488,860 | 1/1970 | Bender et al. | 220/345 |
| 3,987,895 | 10/1976 | Jamshidi | 206/570 |

Primary Examiner—William T. Dixson, Jr.
Attorney, Agent, or Firm—Merchant, Gould, Smith, Edell, Welter & Schmidt

[57] ABSTRACT

A two-tier disposable tray for retaining instruments and other items used in conducting percutaneous transhepatic cholangiographies (PTC's) in an organized and easily accessible manner within a sterile environment. The upper tier slideably engages the lower tier of the tray. The tray and its components are in ready-to-use package form with the package adapted to be opened at the patient's side at the time the PTC is performed.

3 Claims, 4 Drawing Figures

DISPOSABLE SLIDE-STEP PERCUTANEOUS TRANSHEPATIC CHOLANGIOGRAPHY PROCEDURE TRAY

BACKGROUND OF THE INVENTION

The present invention relates to an improved tray for storing, shipping, and retaining instruments and other items necessary for conducting percutaneous transhepatic cholangiography (PTC) procedures in a sterile field or for conducting similar roentgenological visualizations by injection of a contrast medium, with or without suctioning of internal bodily fluids prior to injection. An aspect of the present invention relates to a two-piece slide-step tray assembly composed of an upper and a lower tray, the upper tray containing apparatus for preparing a sterile field, the lower tray containing the instruments necessary to complete a PTC procedure.

As known in the art, the PTC technique visualizes the biliary tree or biliary tract for radiographic examination or the like. It is a valuable tool in the diagnosis of, for example, biliary obstructions or jaundice, and can differentiate surgical from non-surgical conditions. The technique was carried out by Huard and Do-Xuan-Hop as early as 1937; see *Bull. Soc. Med. Chir. Indochine* 15:1090–1100 (1937). Today, the reliability of the PTC technique and its value to surgeons, radiologists, etc. should be considered established, see Seldinger, *Acta Radiol.* (Suppl) 253:1 (1966); Weichel, *Acta Chir. Scand.* (Suppl) 380:1 (1964); and Redeker, et al, *JAMA* 231:386 (1975).

Before conducting a PTC procedure, it is necessary that a sterile field be created. It is necessary to utilize separate materials for the different phases of the overall procedure, including the materials used to establish a sterile field and those materials used for the actual taking of a specimen. In the past, separate trays have been used sequentially, the first tray being employed to establish the steril field, the second tray containing the instruments necessary to perform the actual procedure. The use of an upper and a lower nested pair of trays for use in performing biopsy (as opposed to cholangiography) procedures is known in the art. See U.S. Pat. No. 3,987,895, issued Oct. 26, 1976. The upper tray of the nested pair contains the material necessary to establish a sterile zone while the lower tray contains the apparatus for performing the actual biopsy. A nested tray arrangement of this type allows the upper tray and materials to be discarded when the sterile field has been established and before the actual procedure is begun. The tolerance between the upper and the lower nested trays of the type described in U.S. Pat. No. 3,987,895 must be closely controlled since if the fit between the two trays is too tight the two trays may stick together while if the fit is too loose the top tray can fall out if the trays are inverted during shipment or if they are dropped during usage, causing the materials in both trays to be spilled.

A wide variety of tray structures are known in the art of surgery, diagnostic techniques, and other relatively unrelated fields such as food packaging or support. The biopsy procedure tray disclosed in the aforementioned U.S. Pat. No. 3,987,895 and the references cited in the file history thereof are believed to be illustrative of the state of the art; see, for example, U.S. Pat. No. 3,467,247 (Weiss), issued Sept. 16, 1969, U.S. Pat. No. 3,329,261 (Serany et al), issued July 4, 1967, and U.S. Pat. No. 3,567,067 (Weiss), issued Mar. 2, 1971.

SUMMARY OF THE INVENTION

The present invention is a two-member disposable slide-step PTC procedure tray. The upper tray contains materials for establishing a sterile field and the lower tray contains the actual materials which are required to perform the PTC procedure. The upper tray slideably engages the top of the lower tray, thus enclosing the top of the lower tray and preventing materials contained therein from falling out when the upper tray is in place and the two-tray combination is inverted. Both trays are generally rectangular and generally planar except for the article holding recesses formed therein. A sterile package including the two-member tray and instruments and materials located therein is supplied to the medical practitioner.

DETAILED DESCRIPTION OF A PREFERRED EMBODIMENT

Figure 1:
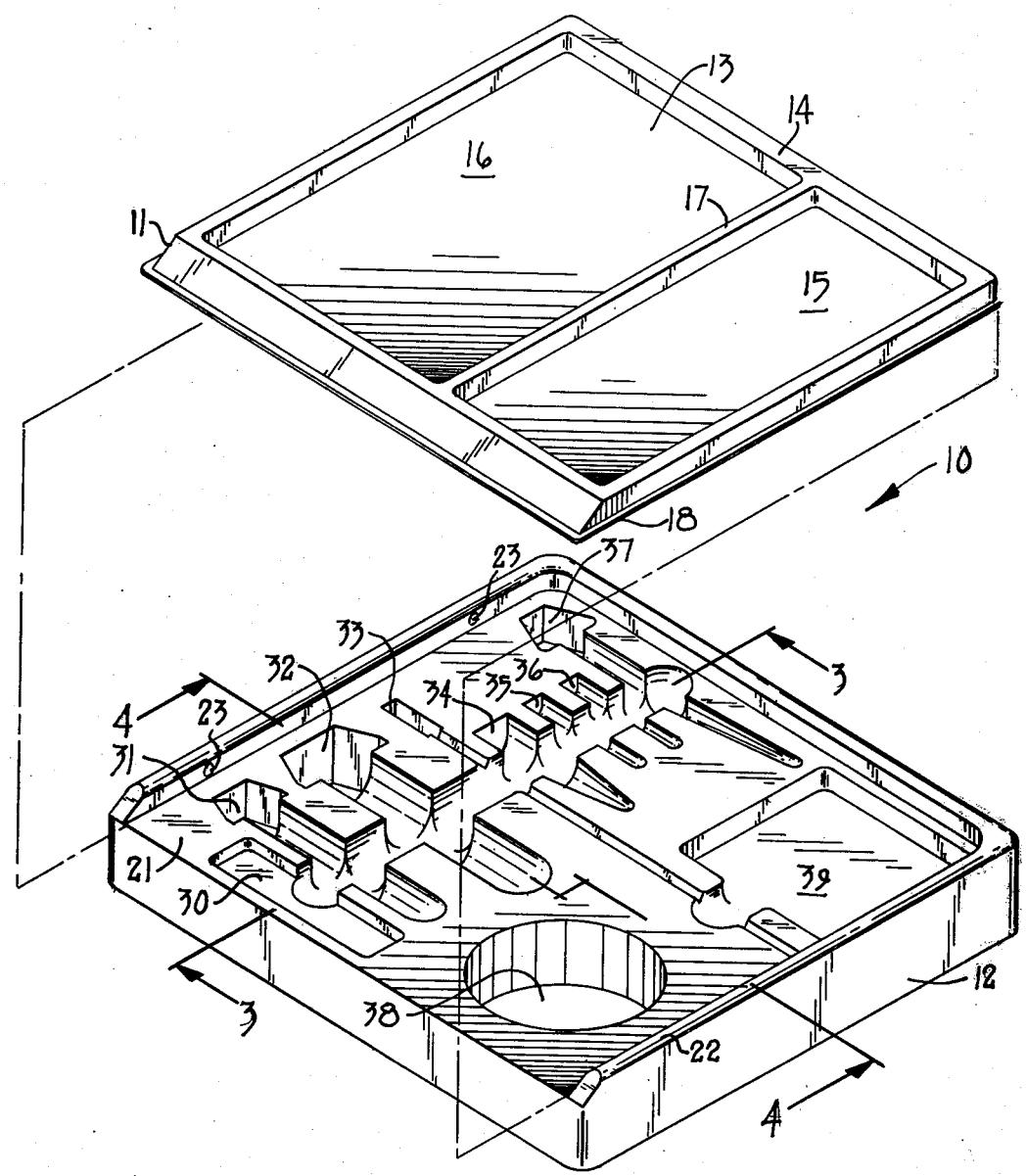
FIG. 1 is an exploded perspective view of the two-member disposable slide-step PTC procedure tray of this invention.
Figure 2:
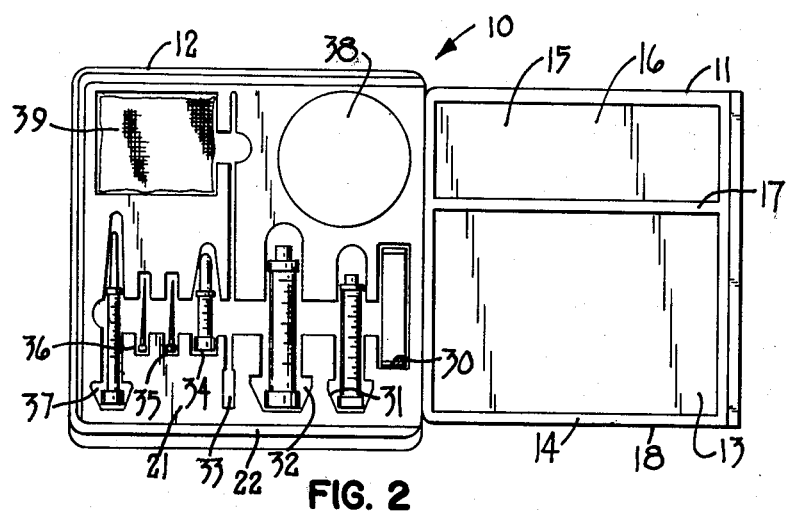
FIG. 2 is a top plan view of the two trays in side-to-side relationship, including the materials contained in the lower tray.
Figure 3:
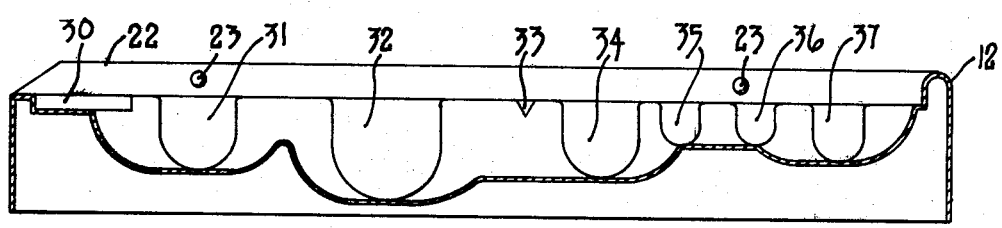
FIG. 3 is a cross-sectional view, taken along line 3—3 of FIG. 1.
Figure 4:
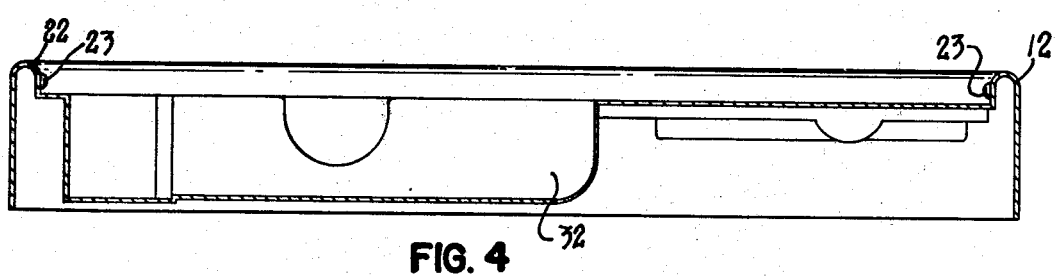
FIG. 4 is a cross-sectional view taken along line 4—4 of FIG. 1.

Referring to the FIGURES wherein like numerals represent like parts throughout the several views, a preferred embodiment of the disposable slide-step PTC procedure tray of this invention is generally shown by the numeral 10 in FIGS. 1 and 2. Disposable slide-step PTC procedure tray 10 includes upper tray member 11 and lower tray member 12.

Upper tray member 11 includes upper tray member top surface 13 which is surrounded by upper tray member peripheral rim 14. Top surface 13 is divided into two article supporting recesses 15 and 16 by divider 17. Article supporting recess 15 normally retains premoistened swabs. Article supporting recess 16 normally retains two surgical drapes. Extending outwardly from peripheral rim 14 is flange 18. As illustrated in FIG. 1, upper tray member 11 is generally planar and generally rectangular.

Lower tray member 12 includes generally rectangular and generally planar lower tray member top surfaces 21 which has a plurality of article supporting recesses formed therein. Top surface 21 of lower tray member 12 is surrounded on three sides by lower tray member peripheral rim 22. The inside of peripheral rim 22 includes flange retaining or boss members 23. The outside of peripheral rim 22 extends downward from the top of the rim to a generally flat plane below the deepest of the supporting recesses formed in lower tray member 12.

The article supporting recesses formed in top surfaces 21 of lower tray member 12 are designed to retain those instruments and the like which are necessary for the actual PTC procedure. Specifically, in the PTC procedure tray as illustrated in the drawings, article supporting recess 30 normally retains an adhesive bandage. Article supporting recess 31 normally retains a 10cc syringe. Article supporting recess 32 normally retains a 20cc syringe. Article supporting recess 33 normally retains a 6 inch or an 8 inch Chiba (trademark) needle.

Article supporting recess 34 normally retains a 5cc ampule of 1% Xylocaine (trademark) hydrochloride or the like. Article supporting recess 35 normally retains a 20×1½ inch needle. Article supporting recess 36 normally retains a 25×⅝ inch needle. Article supporting recess 37 normally retains a 3cc syringe with a 20×1½ inch needle. Article supporting recess 38 normally retains a 3-way stopcock and tubing. Article supporting recess 39 normally retains gauze pads.

Prior to using disposable slide-step PTC procedure tray 10, i.e. during storage or shipment, lower tray member 12 normally slideably engages upper tray member 11. Upper tray member 11 engages lower tray member 12 by sliding flange 18 along lower tray member top surface 21 causing flange 18 to slide between flange retaining members 23 and lower tray member top surface 21. Upper tray member 11 slides on lower tray member 12 from the side of lower tray member 12 along which lower tray member peripheral rim 22 does not extend. When upper tray member 11 completely engages lower tray member 12, the instruments in lower tray member 12 are completely confined and concealed. This allows the surgeon to sequentially perform a PTC procedure by initially forming a sterile field while protecting the instruments and materials which are required for the actual PTC procedure from exposure during the preparation of the sterile field.

Prior to shipment, all of the instruments, materials, and both trays are sterilized, e.g. by ethylene oxide sterilization or the like. The sterilized instruments and materials can then be packaged in individual sterile packages, e.g. in a heat-sealed impermeable polymeric film, which are placed in the appropriate article supporting recesses.

Typical PTC procedures have been carried out on literally hundreds of patients with hepatobiliary disease, using a very thin needle. Visualization of the biliary tree can be accomplished without suctioning of the bile. Complications are relatively infrequent.

In this invention, the assembled PTC tray is placed on any suitable horizontal support. After using swabs and drapes or the like stored in the upper tray member 11, upper tray member 11 is removed exposing lower tray member 12. The supine patient is locally anesthetized by injection with 1% xylocaine hydrochloride or the like as far as the peritoneum. The needle is introduced in the conventional manner from, for example, the seventh or eighth interspace, and the needle insertion is made parallel to the plane of the table on which the patient is lying. The puncture site can be, for example, 10-13 centimeters from the table, depending on the patient's chest thickness. After anesthetizing the needle's course, the stylet is removed, and the needle is connected to a 3-way stopcock which is connected to the syringe and to the source of the contrast medium. The stopcock is then appropriately positioned to first fill the syringe and then to inject the patient. When the medium successfully enters a bile duct, the X-ray pictures are taken. After the pictures are taken, the needle can be removed. Disposable needles can then be discarded, along with the disposable tray member.

The advantages of using a two-tier tray for a PTC procedure will now be evident to those skilled in the art. The instruments (the needle, etc.) need not ever contact the horizontal support and are stored in and removed from the sterile lower tray member 12. Disposable tray members and instruments simplify sterilization procedures. The chance of incorrectly carrying out the procedure is reduced.

What is claimed is:

1. A two-member disposable slide-step roentgenological visualization procedure tray for sequentially performing sterile procedures comprising a one-piece lower tray member and a one-piece upper tray member;
   (a) said one-piece lower tray member comprising:
      (1) a lower tray member top surface having a generally rectangular periphery and being generally planar except for a plurality of article supporting recesses formed therein;
      (2) an integral outer peripheral upwardly extending rim-like retaining means surrounding three sides of said lower tray member top surface, and defining an area for the receiving of said one-piece upper tray member in a position juxtaposed upon said lower tray member top surface; said rim-like retaining means extending upwardly from said lower tray member top surface;
      (3) an integral, three-sided downwardly depending flange means extending downwardly from the top of said rim-like retaining means down to a generally flat plane below the lowest portion of the deepest or most downwardly extending article supporting recesses to provide a bottom edge serving as an open base for supporting said lower tray member;
      (4) a plurality of boss means in said rim-like retaining means spaced above said lower tray member top surface to retain said upper tray member in said area defined by said rim-like retaining means while permitting transversely sliding movement of said upper tray member with respect to said top surface of said lower tray member; and
   (b) said one-piece upper tray member being in a juxtaposed position upon said lower tray member top surface and transversely slideably removeable from said juxtaposed position and comprising:
      (1) a generally planar, generally rectangular article-supporting upper tray member top surface having a smaller area than said lower tray member top surface;
      (2) an integral peripheral rim surrounding the periphery of said upper tray member top surface and extending upwardly from said upper tray member top surface, the area defined by said peripheral rim being smaller than the area defined by said rim-like retaining means, whereby said peripheral rim fits within said area defined by said rim-like retaining means in closely spaced relation to said rim-like retaining means;
      (3) outwardly extending flange means extending outward from said rim to provide a generally peripheral flat planar surface extending outwardly beyond the area of said upper tray member top surface, for positioning below said boss means while said upper tray member is in said juxtaposed position, and for permitting sliding transverse movement of said upper tray member transversely with respect to said lower tray member top surface.

2. Procedure tray having upper and lower tray members according to claim 1, wherein said procedure tray contains instruments and materials and is packaged within a polymeric film package, said procedure tray, instruments, and materials having been subjected to ethylene oxide sterilization.

3. Procedure tray having upper and lower tray members according to claim 1, wherein the top surface of said lower tray includes a plurality of syringe- and needle-supporting recesses; all of the syringe- and needle-supporting recesses being interconnected with each other.

* * * * *